(12) United States Patent
Shanghvi et al.

(10) Patent No.: US 7,964,216 B2
(45) Date of Patent: Jun. 21, 2011

(54) SPACED DRUG DELIVERY SYSTEM

(75) Inventors: Dilip Shantilal Shanghvi, Mumbai (IN); Kirti Wardhaman Ganorkar, Mumbai (IN); Yashoraj Rupsinh Zala, Mumbai (IN); Nitin Bhalachandra Dharmadhikari, Mumbai (IN); Satish C Khanna, Basle (CH)

(73) Assignee: Sun Pharma Advanced Research Company Limited, Mumbai (IN)

( * ) Notice: Subject to any disclaimer, the term of this patent is extended or adjusted under 35 U.S.C. 154(b) by 1007 days.

(21) Appl. No.: 10/466,036

(22) PCT Filed: Jan. 11, 2002

(86) PCT No.: PCT/IN02/00005
§ 371 (c)(1), (2), (4) Date: Nov. 17, 2003

(87) PCT Pub. No.: WO02/055009
PCT Pub. Date: Jul. 18, 2002

(65) Prior Publication Data
US 2004/0086562 A1    May 6, 2004

(30) Foreign Application Priority Data

Jan. 12, 2001 (IN) .............................. 37/MUM/2001
Apr. 10, 2001 (IN) .......................... 323/MUM/2001
Apr. 10, 2001 (IN) .......................... 324/MUM/2001
Apr. 10, 2001 (IN) .......................... 325/MUM/2001
Apr. 10, 2001 (IN) .......................... 326/MUM/2001

(51) Int. Cl.
*A61K 9/20* (2006.01)
*A61K 9/22* (2006.01)
*A61K 9/24* (2006.01)
*A61K 9/26* (2006.01)

(52) U.S. Cl. ........ 424/472; 424/464; 424/468; 424/469; 424/470

(58) Field of Classification Search .................. None
See application file for complete search history.

(56) References Cited

U.S. PATENT DOCUMENTS

| | | | |
|---|---|---|---|
| 3,247,066 A | 4/1966 | Milosovich, Jr. | |
| 4,252,786 A | 2/1981 | Weiss et al. | |
| 4,524,060 A | 6/1985 | Mughal et al. | |
| 4,681,583 A | 7/1987 | Urquhart et al. | |
| 4,857,336 A * | 8/1989 | Khanna et al. | |
| 4,871,549 A | 10/1989 | Ueda et al. | |
| 4,874,388 A * | 10/1989 | Wong et al. | |
| 4,891,223 A | 1/1990 | Ambegaonkar et al. | |
| 4,976,967 A | 12/1990 | McClelland et al. | |
| 5,162,117 A | 11/1992 | Stupak et al. | |
| 5,188,841 A * | 2/1993 | Simpkin et al. ............... 424/495 |
| 5,209,746 A | 5/1993 | Balaban et al. | |
| 5,226,902 A * | 7/1993 | Bae et al. | |
| 5,229,131 A | 7/1993 | Amidon et al. | |
| 5,260,069 A | 11/1993 | Chen | |
| 5,474,784 A | 12/1995 | Stevens et al. | |
| 5,795,591 A * | 8/1998 | Lee et al. | |
| 5,840,329 A * | 11/1998 | Bai ............................... 424/458 |
| 5,882,656 A | 3/1999 | Bechard et al. | |
| 6,004,582 A * | 12/1999 | Faour et al. ................... 424/473 |
| 6,011,049 A | 1/2000 | Whitcomb | |
| 6,031,004 A | 2/2000 | Timmins et al. | |
| 6,056,977 A * | 5/2000 | Bhagwat et al. ............. 424/488 |
| 6,096,341 A * | 8/2000 | Seth ............................... 424/482 |
| 6,099,862 A | 8/2000 | Chen et al. | |
| 6,117,450 A | 9/2000 | Dittgen et al. | |
| 6,153,632 A | 11/2000 | Rieveley | |
| 6,166,043 A | 12/2000 | Ikeda et al. | |
| 6,172,090 B1 | 1/2001 | Ikeda et al. | |
| 6,217,904 B1 * | 4/2001 | Midha et al. .................. 424/468 |
| RE37,330 E | 8/2001 | Barelli et al. | |
| 6,352,721 B1 | 3/2002 | Faour | |
| 6,475,521 B1 * | 11/2002 | Timmins et al. ............. 424/469 |
| 6,491,949 B2 | 12/2002 | Faour et al. | |

(Continued)

FOREIGN PATENT DOCUMENTS

DE    3629994 A1    3/1988

(Continued)

OTHER PUBLICATIONS

International Search Report of PCT/IN02/00107, U.S. Appl. No. 10/474,360 ('360 application).
International Search Report of PCT/IN2004/000092, U.S. Appl. No. 10/551,456 ('456 application).
International Search Report of PCT/IN02/00107, U.S. Appl. No. 10/474,360 ('360 application), 2002.*
International Search Report of PCT/IN2004/000092, U.S. Appl. No. 10/551,456 ('456 application), 2004.*

*Primary Examiner* — S. Tran
(74) *Attorney, Agent, or Firm* — Westerman, Hattori, Daniels & Adrian, LLP

(57) ABSTRACT

The present invention provides to a method of administration of two or more therapeutically active agents comprising orally administering to a patient a spaced drug delivery system, wherein the time of release of the two or more therapeutically active agents is designed to provide desired control on the disease condition. The present invention also provides a method of administration of two or more therapeutically active agents comprising orally administering to a patient a spaced drug delivery system at a specified time prior to food intake by the patient. The present invention further provides a spaced drug delivery system that releases two or more antidiabetic agents at different times after oral administration, for the treatment of diabetes mellitus or conditions associated with diabetes mellitus. More particularly, the present invention provides a spaced drug delivery system that immediately releases one or more antidiabetic agents after oral administration of the system, and releases as a pulse one or more antidiabetic agents in a reliable manner at about a predetermined time after oral administration of the system.

15 Claims, No Drawings

U.S. PATENT DOCUMENTS

| | | |
|---|---|---|
| 6,632,451 B2 * | 10/2003 | Penhasi et al. ............... 424/464 |
| 6,787,531 B1 * | 9/2004 | Hilman et al. ............... 514/171 |
| 2002/0041904 A1 * | 4/2002 | Yamahara ............... 424/725 |
| 2002/0099361 A1 * | 7/2002 | Faour ............... 604/892.1 |
| 2002/0136744 A1 * | 9/2002 | McGlynn et al. |
| 2004/0156900 A1 | 8/2004 | Shanghvi et al. |
| 2006/0210633 A1 * | 9/2006 | Dharmadhikari et al. |
| 2007/0071820 A1 | 3/2007 | Prater et al. |

FOREIGN PATENT DOCUMENTS

| | | |
|---|---|---|
| EP | 0396404 A1 | 11/1990 |
| EP | 0427519 A2 | 5/1991 |
| EP | 0549331 A1 | 6/1993 |
| EP | 1095650 A1 | 5/2001 |
| EP | 1 123 700 | 8/2001 |
| IE | 902533 | 2/1991 |
| JP | 60-241871 A * | 11/1985 |
| WO | 98/56378 | 12/1998 |
| WO | 98/57634 | 12/1998 |
| WO | 98/57649 | 12/1998 |
| WO | WO 9857649 A1 * | 12/1998 |
| WO | 99/03476 | 1/1999 |
| WO | 99/03477 | 1/1999 |
| WO | 99/03478 | 1/1999 |
| WO | 99/18938 | 4/1999 |
| WO | 00/25757 A1 | 5/2000 |
| WO | 00/28989 | 5/2000 |
| WO | WO 0028989 A1 * | 5/2000 |
| WO | 00/74655 | 12/2000 |
| WO | 02/11702 A2 | 2/2002 |

* cited by examiner

SPACED DRUG DELIVERY SYSTEM

FIELD OF THE INVENTION

The present invention relates to a method of administration of two or more therapeutically active agents comprising orally administering to a patient a spaced drug delivery system wherein the time of release of the two or more therapeutically active agents is designed to provide desired control on the disease condition The present invention also relates to a method of administration of two or more therapeutically active agents comprising orally administering to a patient a spaced drug delivery system at a specified time prior to food intake by the patient.

The present invention also relates to a spaced drug delivery system that releases two or more antidiabetic agents at different times after oral administration, for the treatment of diabetes mellitus or conditions associated with diabetes mellitus.

More particularly, the present invention relates to a spaced drug delivery system that immediately releases one or more antidiabetic agents after oral administration of the system, and releases as a pulse one or more antidiabetic agents in a reliable manner at about a predetermined time after oral administration of the system.

BACKGROUND OF THE INVENTION

Patients are often required to take multiple medications for the prophylaxis or treatment of diseases. Often patients are required to take different medications at different specified times. This results in patient inconvenience and consequently patient non-compliance to the prescribed dosage regimen.

A combination of two different medications could be taken at specified different times to obtain the desired control on the symptoms of the disease or a measurable indicator of the disease condition. For example, a specific antidiabetic agent may be orally administered at a specific time period prior to food intake to control post-prandial glucose and a second antidiabetic agent may be more useful in controlling glucose levels when given with food. However, there are no prior art spaced drug delivery systems that enable one to administer medications in a convenient manner. Thus, there is a need for a method of administration of two or more therapeutically active agents comprising orally administering to a patient a spaced drug delivery system, wherein at least one first therapeutically active agent is released immediately upon oral administration of the spaced drug delivery system and at least one second therapeutically active agent is released as a pulse at a predetermined time after oral administration, wherein the two or more therapeutic agents act on the disease condition by similar or dissimilar, but complementary mechanisms, to control the symptoms of the disease, or a measurable indicator of the disease condition, and further wherein the time of release of the two or more therapeutically active agents is designed to provide desired control on the disease condition.

A combination of two different medications could also be taken at specified different times when one medication is required to be given on an empty stomach and the other with meals. Reasons for giving certain medications on an empty stomach or with meals are well known to those skilled in the art and include for example, different rate or extent of absorption of the drug on an empty stomach versus in presence of food, difference in extent of degradation of the drug in gastric fluids when given with food versus without food, gastric irritation due to the drug and thus, there is a need for a method of administration of two or more therapeutically active agents comprising orally administering to a patient a spaced drug delivery system at a specified time prior to food intake by the patient, wherein at least one therapeutically active agent is released immediately upon oral administration of the spaced drug delivery system and at least one therapeutically active agent is released as a pulse after a delay at about the time when food is taken i.e. either immediately prior to meals, or at the time of meals, or after meals.

Maximum reduction in post-prandial blood-glucose can be obtained by administering antidiabetic agents such as glipizide about 30 minutes before meals, and hence, an immediate release of such antidiabetic agents is essential. On the other hand, an antidiabetic agent such as metformin is given with food. A spaced drug delivery system that immediately releases an antidiabetic agent, such as glipizide, after oral administration of the system prior to meals, and releases as a pulse, after a delay, antidiabetic agents such as metformin, at the time the meal is taken, would provide improved patient compliance to the dosage regimen and optimum clinical benefits.

Non-insulin dependent diabetes mellitus (NIDDM), also known as maturity-onset diabetes or diabetes mellitus type 2, is a frequent metabolic disease and the main cause of hyperglycemia. It is a heterogeneous disease with complex, unclarified metabolic aspects. Insulin secretion may appear normal or even excessive, but it is insufficient to compensate for insulin resistance. The disease is characterized by three main abnormalities of metabolism contributing to hyperglycemia. These include the partial or complete decrease in insulin secretion, resistance of the peripheral tissues to insulin and increased hepatic production of glucose in fasting conditions. Insulin resistance may also be responsible for the obesity associated with NIDDM, although obesity itself has a reciprocal effect on insulin resistance; excess weight worsens insulin resistance, while weight loss lowers blood glucose levels. Diet and physical exercise cause a reduction in insulin-resistance and lead to an improvement in the pancreas deficit over a period of time.

The treatment goal of NIDDM is to normalize blood-glucose level in an attempt to prevent or reduce complications that may arise due to chronic hyperglycemia. The effect of regular exercise supplementing diet in patients with NIDDM causes a reduction in insulin-resistance and leads to an improvement in the pancreas deficit over a period of time. When these provisions are not sufficient, a pharmacological agent needs to be taken for control of hyperglycemia. Oral medications work either to reduce the body's resistance to its own insulin, or work to increase insulin secretion to meet the demand. Sulfonylureas and biguanides have been used in oral antidiabetic therapy. Other classes of oral antidiabetic agents include the alpha-glucosidase inhibitors, aldose reductase inhibitors, thiazolidinediones, insulin secretagogues and others. The use of these classes of compounds in monotherapy has been effective in obtaining a glycometabolic control in diabetic patients.

Biguanide derivatives like metformin, phenformin and buformin, generally in the form of their hydrochloride salt, have been used as anti-hyperglycemic agents in the treatment of non-insulin dependent diabetes mellitus. The mechanism of action of the drugs belonging to this class includes reduction in hepatic glucose production, decrease in intestinal absorption of glucose, and increase in glucose uptake and utilization. Biguanides improve glucose tolerance in patients with diabetes mellitus type 2, lowering both basal and post-prandial plasma glucose. With biguanide therapy, insulin secretion remains unchanged while fasting insulin levels and day-long plasma insulin response may actually decrease. Although phenformin is still used widely as an anti-hyperglycemic agent, metformin is the preferred biguanide, as it exerts a better normoglycemic action with a lower risk of lactic acidosis—a common side-effect with phenformin therapy. Metformin is also known to lower blood triglyceride levels and assist in weight reduction.

The sulfonyl ureas used in the treatment of diabetes mellitus type 2 include acetohexamide, carbutamide, chlorpropamide, glipizide, glyburide (glibenclamide), glimepiride, gliclazide, glibomuride, gliquidone, glisoxepid, glyhexamide, phenbutamide, tolazamide, tolbutamide, tolcyclamide, etc. These sulfonyl ureas are used as their bases and not as salts. The mechanism of action of these drugs involves lowering of blood glucose concentration mainly by stimulating release of endogenous insulin from beta cells of the pancreas, and thus they act as hypoglycemic agents. The sulfonyl ureas are used as an adjunct to diet for the management of non-insulin dependent diabetes mellitus in patients whose hyperglycemia cannot be controlled by diet alone. To achieve maximum reduction in post-prandial blood-glucose concentration, the sulfonyl urea is administered 30 minutes prior to each meal.

The $55^{th}$ edition of the Physicians' Desk Reference, copyright 2001, suggests that the monotherapy with metformin hydrochloride, commercially available under the trade name Glucophage® from Bristol-Myers Squibb Co., may be effective in patients who have not responded to sulfonyl ureas or who have only a partial response to sulfonyl ureas or who have ceased to respond to sulfonyl ureas. In such patients, if adequate glycemic control is not attained with Glucophage® monotherapy, the combination of Glucophage® and a sulfonyl urea may have a synergistic effect. Also, monotherapy with the sulfonyl ureas has been found to give a positive response, which lasts for 4-5 years, but it becomes ineffective in a large number of patients over a period of time. This is referred to as the "secondary failure" associated with the oral therapy with hypoglycemic agents. In both these cases, a combination of biguanides and sulfonyl ureas is used. The biguanides are able to act on insulin resistance but cannot stimulate insulin secretion, while the sulfonyl ureas can stimulate insulin release but are unable to act on insulin resistance. A combination therapy of a biguanide and a sulfonyl urea has a synergistic effect on glucose control, since both agents act by different but complementary mechanisms.

Diabetes mellitus is a chronic disease with diverse pathologic manifestations and is accompanied by lipid metabolism disorders and circulatory disorders, as well as glycometabolism disorders. As a result, the disease tends to progress entailing complications in many cases. Therefore, it is necessary to select the drug of choice for the prevailing disease state in each individual case. However, this selection is often difficult in clinical settings because single use of each individual drug cannot bring sufficient effects in some disease states and there are various problems such as side effects caused by an increased dose or long-term administration of a single drug or agent. Hence, there is a need to include combination therapy in NIDDM.

Alpha glucosidases are essential for the breakdown of starches, dextrins, maltose and sucrose. Alpha glucosidase inhibitors act by delaying glucose absorption from a carbohydrate load by inhibiting the glucosidases. The compounds of this class have the ability to prevent or attenuate diabetic nephropathic lesions. The common drugs of this class include acarbose, miglitol, emiglitate and voglibose. Inhibition of alpha glucosidase causes a delay in the digestion of sucrose and other polysaccharides, thus retarding the rate of absorption of glucose and fructose. Acarbose is a complex oligosaccharide, which competitively inhibits intestinal brush border alpha glucosidases including glucoamylase, sucrase, maltase and isomaltase. It is the preferred alpha glucosidase inhibitor for use as an antihyperglycemic because it does not cause hypoglycemia. The drug also has weight lowering action. The alpha glucosidase inhibitors may be administered along with other oral antidiabetic drugs for a better control on the blood-glucose levels. The $55^{th}$ edition of the Physicians' Desk Reference, copyright 2001, states that acarbose diminishes the insulinotropic and weight increasing effects of sulfonyl ureas, when administered together.

The thiazolidinediones is another class of antidiabetic agents which are thought to act by enhancing insulin action, thus promoting glucose utilization in the peripheral tissues, possibly by stimulating non-oxidative glucose metabolism in muscle, and suppressing gluconeogenesis in the liver. The drugs belonging to this class stimulate adipogenesis and reduce plasma triglyceride and free fatty acid concentrations. The examples of thiazolidinediones commonly used in diabetes mellitus include troglitazone, pioglitazone, rosiglitazone, ciglitazone, darglitazone and englitazone. Although thiazolidinediones enhance insulin action at the cellular level, they do not stimulate insulin release nor do they mimic its action. The therapeutic benefits of thiazolidinedione treatment depend on the availability of adequate amounts of insulin. The addition of a thiazolidinedione antidiabetic agent to concurrent sulfonyl urea treatment provides a balance of stimulated release of insulin while ameliorating insulin resistance.

A new class of insulinotropic agents (secretagogues) called metglitinide analogs or prandial glucose regulators, is now being used in the management of NIDDM. The compounds of this class are fast acting, short acting, non-sulfonyl urea, oral hypoglycemic agents that act by regulating prandial glucose. The prandial glucose regulation is aimed at restoring the first-phase insulin response that follows consumption of a meal, which is missing in NIDDM patients. Repaglinide, the most commonly used agent of this class, provides a tighter glycemic control, while reducing the risk of hypoglycemic events. The drug lowers blood-glucose levels by stimulating the secretion of insulin from the pancreas. This action is dependent on the functioning β-cells in the pancreatic islets. Repaglinide closes ATP-dependent potassium channels in the β-cell membrane by binding at characterisable sites. This potassium channel blockade depolarizes the β-cell, which leads to an opening of calcium channels. The resulting increased calcium influx induces insulin secretion. The ion-channel mechanism is highly tissue selective, with low affinity for heart and skeletal muscle. Repaglinide is rapidly absorbed and rapidly eliminated, ensuring quick return of post-prandial insulin levels to preprandial levels. Insulin release is glucose dependent and diminishes at low glucose concentrations. Repaglinide also offers increased mealtime flexibility and safety. As a result of the short plasma half-life and lack of accumulation of repaglinide with repeated dosing, the risk of between-meal and nocturnal hypoglycemia is substantially reduced. The drug acts synergistically with biguanides and thiazolidinediones, especially metformin and troglitazone. The dose of repaglinide ranges from 0.5 to 4 mg, administered before each meal.

The prior art includes a number of systems that use a combination of antidiabetic agents for the treatment of non-insulin dependent diabetes mellitus. U.S. Pat. No. RE 37330 (a reissue of U.S. Pat. No. 5,922,769) claims a method of treating non-insulin dependent diabetes mellitus in cases of secondary failure to a treatment utilizing a combination of glibenclamide-metformin hydrochloride, in a weight ratio higher than 1:100, comprising administering to a subject in need of same a combination of glibenclamide and metformin, expressed as the hydrochloride, in a weight ratio of 1:100. The patent also discloses the results of a clinical study, which indicates that the maximum dose of glibenclamide, which does not cause any side-effects, is 15 mg/day, while that for metformin is 1500 mg/day, and that the use of such a combination in a ratio lower than that claimed would result in formulations that do not attain the optimum therapeutic effect. The patent claims the combination of glibenclamide and metformin in a tablet form. The patent does not disclose a formulation wherein the sulfonyl urea is released immediately and the biguanide is released after a delay period, particularly after a predetermined delay period.

U.S. Pat. No. 6,031,004 ('004) discloses the use of a combination of novel salts of metformin and glyburide, in the treatment of diabetes mellitus type 2. In this invention, both metformin salt and glyburide are released immediately. The patent does not disclose a composition wherein the sulfonyl urea is released immediately and the biguanide is released after a delay period, particularly after a predetermined delay period.

U.S. Pat. No. 6,099,862 ('862) claims a controlled release pharmaceutical tablet which consists essentially of (a) a core consisting essentially of: (i) metformin or a pharmaceutically acceptable salt thereof, (ii) glipizide, (iii) polyvinylpyrrolidone, and (iv) sodium lauryl sulfate, (b) optionally a seal coat around the core, (c) a semipermeable membrane coating covering said core comprising—(i) cellulose acetate, (ii) polyethylene glycol with an average molecular weight between 380 and 420, and (iii) a plasticiser, and (d) at least one passageway in the semipermeable membrane to allow the release of the metformin and glipizide from the core to the environment of use to provide therapeutic levels of metformin and glipizide from twelve to twenty-four hour periods. In this invention, both metformin salt and glipizide are released slowly upon oral administration. The patent does not disclose a composition wherein the sulfonyl urea is released immediately and the biguanide is released after a delay period, particularly after a predetermined delay period.

PCT applications WO 98/57649 and WO 99/03476 both claim a combination of an insulin sensitiser such as a thiazolidinedione and an insulin secretagogue such as a sulfonyl urea. The system of the PCT application WO 99/03477 claims a method for the treatment of diabetes mellitus and conditions associated with it, using a combination of an insulin sensitiser, an insulin secretagogue and a biguanide antihyperglycemic agent. The insulin sensitiser used in this combination is a thiazolidinedione like troglitazone, ciglitazone, rosiglitazone, pioglitazone or englitazone, and the insulin secretagogue is a sulfonyl urea or repaglinide. The application thus claims the combination of a thiazolidinedione, a sulfonyl urea or repaglinide, and a biguanide. The application discloses that the claimed combinations exhibit synergism when given as a unit dosage form, and therefore the amount of each agent required is reduced. However, all the agents are released in a conventional manner, thereby reducing the flexibility of administration.

PCT application WO 99/03478 claims a method for the treatment of diabetes mellitus and conditions associated with it, using a combination of an insulin sensitiser, an insulin secretagogue and an alpha glucosidase inhibitor. The insulin sensitiser used is a thiazolidinedione, the insulin secretagogue is a sulfonyl urea or repaglinide, while the alpha glucosidase inhibitor is selected from acarbose, emiglitate and miglitol. The application discloses that such a combination has a beneficial effect on the glycemic control as a result of a synergistic effect, and also has minimum side effects. The invention, however, does not provide spaced drug delivery of a combination of two or more antidiabetic agents, wherein one antidiabetic agent is released immediately and the other antidiabetic agent(s) is/are released at a predetermined time interval.

The system of the U.S. Pat. No. 6,011,049 claims a composition comprising a combination of synergistic amounts of a sulfonyl urea, a thiazolidinedione (glitazone) antidiabetic agent and a biguanide. The patent teaches that since the unstimulated insulin secretory capacity of the β-cells is very low in NIDDM, reversing insulin resistance alone would be of partial benefit. Therefore, the system maintains a level of stimulated insulin secretion with a sulfonyl urea while adding glitazone to improve insulin sensitivity, thereby providing a level of glycemic control unattainable by either medication alone. However, the invention does not provide a spaced drug delivery system of a combination of the two or more antidiabetic agents.

The system claimed in the PCT application WO 98/56378 uses a short-acting hypoglycemic agent capable of stimulating insulin secretion from β-cells, for the manufacture of a medicament adapted to stimulate meal-related insulin secretion, for the treatment of post-prandial hyperglycemia in NIDDM patients. The system uses repaglinide or a combination of repaglinide with long-acting hypoglycemic agents like metformin, a sulfonyl urea or troglitazone. The application teaches that repaglinide stimulates endogenous secretion of insulin in connection with meals, while metformin enhances tissue sensitivity towards insulin, the combination providing a significant improvement in glycemic control. The combination is administered prandially. The invention, however, does not provide spaced drug delivery of a combination of two or more antidiabetic agents, wherein one antidiabetic agent is released immediately and the other antidiabetic agent(s) is/are released at a predetermined time interval.

U.S. Pat. No. 6,166,043 ('043) claims a method for reducing the amounts of active components administered to a diabetic patient, which comprises administering a therapeutically effective amount of an insulin sensitivity enhancer in combination with a biguanide. The insulin sensitivity enhancer claimed in the system is a thiazolidinedione selected from pioglitazone and troglitazone, while the biguanide is selected from metformin, phenformin and buformin. The combination is administered as an admixture or the agents are administered independently, wherein both the agents are released immediately.

U.S. Pat. No. 6,172,090 ('090) claims a method for reducing side effects of active components administered to a diabetic patient, which comprises administering to the said patient a therapeutically effective amount of an insulin sensitivity enhancer in combination with a biguanide. Similar to the '043 system, the patent claims a combination of a thiazolidinedione like pioglitazone or troglitazone, and a biguanide like metformin, phenformin or buformin, which is administered independently or as an admixture. In this invention, the thiazolidinedione and the biguanide are available immediately after oral administration of the dosage form as a conventional release.

U.S. Pat. No. 6,153,632 ('632) claims a composition for the treatment of diabetes mellitus comprising a therapeutic amount of an insulin sensitiser and a therapeutic amount of an antidiabetic agent, the latter being selected from the group consisting of orally ingestible insulin, injectable insulin, a sulfonyl urea, a biguanide and an alpha glucosidase inhibitor. The insulin sensitiser used in the invention is a thiazolidinedione. Both the antidiabetic agents are released immediately after oral administration of the composition in a conventional manner.

PCT application WO 98/57634 ('634) claims a method for treating diabetes mellitus and conditions associated with it comprising administering an effective non-toxic and pharmaceutically acceptable amount of an insulin sensitiser and a biguanide antihyperglycemic agent. The insulin sensitiser used in the invention is a thiazolidinedione. In this invention both the antidiabetic agents are released immediately.

PCT application WO 00/28989 claims a pharmaceutical composition comprising an insulin sensitiser and another antidiabetic agent, and a pharmaceutically acceptable carrier therefore, wherein the composition is arranged to provide a modified release of at least one of the insulin sensitiser and the other antidiabetic agent. The modified release claimed may be a delayed release using gastric resistant formulation, or a sustained release using disintegrating, non-disintegrating or eroding matrices, or a controlled release formulation. The insulin sensitiser used in the invention is a thiazolidinedione, while the other antidiabetic agent is selected from an alpha glucosidase inhibitor, biguanide and an insulin secretagogue, the insulin secretagogue being a sulfonyl urea, repaglinide or nateglinide. The application teaches that the combination provides an advantageous delivery of the antidiabetic agents, maintaining effective glycemic control and has no observed adverse effects. The invention, however, does not provide spaced drug delivery of a combination of two or more antidiabetic agents, wherein one antidiabetic agent is released immediately and the other antidiabetic agent(s) is/are released at a predetermined time interval.

A plethora of prior arts relate to pharmaceutical compositions that release a drug after a delay. Some prior arts that relate to release of drug after a predetermined time include U.S. Pat. No. 3,247,066; Irish patent application no IE 902533; U.S. Pat. Nos. 4,871,549; 5,229,131; PCT Publication no WO 99/18938 and PCT Publication no WO 00/74655. All of these relate to systems comprising a core that swells upon imbibing fluid from the surrounding and a coat that ruptures due to the pressure exerted upon it by the swelling core. However, none of these prior arts disclose a spaced drug delivery system designed to provide desired control on the disease condition, comprising
   a. a first composition comprising one or more first therapeutically active agents, and
   b. a second composition comprising one or more second therapeutically active agents,
wherein at least one first therapeutically active agent is released immediately upon oral administration of the spaced drug delivery system, and at least one second therapeutically active agent is released as a pulse at a predetermined time after oral administration, wherein the two or more therapeutic agents act on the disease condition by similar or dissimilar, but complementary mechanisms, to control the symptoms of the disease, or a measurable indicator of the disease condition, and further wherein the time of release of the two or more therapeutically active agents is designed to provide desired control on the disease condition. More specifically and particularly, none of the prior arts suggest that it would benefit the treatment of diabetes mellitus by oral administration of a spaced drug delivery system comprising one or more therapeutically active antidiabetic agents wherein at least one first therapeutically active antidiabetic agent is released immediately upon oral administration of the spaced drug delivery system, and at least one second therapeutically active antidiabetic agent is released as a pulse at a predetermined time after oral administration. Further, they do not disclose a spaced drug delivery system that immediately releases at least one first therapeutically active agent after oral administration of the spaced drug delivery system at a specified time prior to meals and releases at least one second therapeutically active antidiabetic agent at about the time the meal is taken. Prior arts such as U.S. Pat. No. 3,247,066, European Patent Application 1123700, U.S. Pat. Nos. 5,260,069, and 4,871,549 are distinct from the present invention in that they relate to controlled release dosage forms. Herein the dose of the drug is divided in multiple units and there is no specific and particular requirement of assurance that a unit ruptures at a predetermined time in a reliable manner. Statistically, different units rupture at different times and thereby provide controlled release of the active ingredient, on an average, over a period of time. In the present invention, the total amount of active ingredient is contained in one single unit and is intended to be released at the predetermined time. An important requirement for using such systems in a large number of patients is that the system should deliver the drug at about the predetermined time in a reliable manner to the large number of patients to whom the system is administered. Thus, the coat rupture should occur reliably and consequently drug should be released reliably. For instance, if in five to ten out of a hundred times the coatings do not open or rupture at about the predetermined time, but rupture at a significantly prolonged time when tested by agitation over a range of agitational conditions and aqueous compositions, then the desired release at the predetermined time is not achieved reliably. Also, if the release prior to rupture may be influenced by changes in pH, then the desired release at the predetermined time is not achieved reliably. Also, if the coat rupture occurs but the therapeutically active agent is not released as a pulse in all or some of the units, then the desired release as a pulse at a predetermined time is not achieved reliably. Prior arts such as WO 99/18938, WO 00/74655, and IE 902533 make no reference to reliability of rupture or release from a large number of tablets or to the process for optimizing the compositions to obtain the reliability of rupture or reliability of release over a large number of tablets. U.S. Pat. No. 5,229,131 presents a large amount of data giving the percent tablets splitting at 30 min and 60 min and the percent tablets releasing their contents at 60 min and 120 min in Tables 12 to 18. The tablets do not provide reliable manner of rupture as provided by the composition of the present invention, wherein 36 out of 36 tablets rupture within ±50% of the coating failure time. Despite the plethora of prior art, there are no commercially successful systems that provide spaced drug delivery in a reliable manner.

The prior art does not mention any formulations or systems containing combinations of two or more therapeutically active antidiabetic agents, wherein at least one therapeutically active antidiabetic agent is released immediately and at least one therapeutically active agent is released after a lag period or a predetermined spacing interval.

OBJECT OF THE INVENTION

It is an object of the present invention to provide a method of administration of two or more therapeutically active agents comprising orally administering to a patient a spaced drug delivery system wherein at least one first therapeutically active agent is released immediately upon oral administration of the spaced drug delivery system and at least one second therapeutically active agent is released as a pulse at a predetermined time after oral administration, wherein the two or more therapeutic agents act on the disease condition by similar or dissimilar, but complementary mechanisms, to control the symptoms of the disease, or a measurable indicator of the disease condition, and further wherein the time of release of the two or more therapeutically active agents is designed to provide desired control on the disease condition.

It is another object of the present invention to provide a method of administration of two or more therapeutically active agents comprising orally administering to a patient a spaced drug delivery system at a specified time prior to food intake by the patient, wherein at least one therapeutically active agent is released immediately upon oral administration of the spaced drug delivery system, and at least one therapeutically active agent is released, as a pulse, after a delay at about the time when food is taken.

It is a particular object of the present invention to provide above referred methods for the administration of two or more therapeutically active antidiabetic agents.

It is an object of the present invention to provide a spaced drug delivery system designed to provide desired control on the disease condition, comprising
  a. a first composition comprising one or more first therapeutically active agents, and
  b. a second composition comprising one or more second therapeutically active agents,
wherein at least one first therapeutically active agent is released immediately upon oral administration of the spaced drug delivery system, and at least one second therapeutically active agent is released as a pulse at a predetermined time after oral administration, wherein the two or more therapeutic agents act on the disease condition by similar or dissimilar, but complementary mechanisms, to control the symptoms of the disease, or a measurable indicator of the disease condition, and further wherein the time of release of the two or more therapeutically active agents is designed to provide desired control on the disease condition.

It is yet another particular object of the present invention to provide a spaced drug delivery system for the treatment of diabetes mellitus or conditions associated with diabetes mellitus, comprising
  a. a first composition comprising one or more therapeutically active antidiabetic agent(s), which is/are released as a pulse after a delay, and
  b. a second composition comprising one or more therapeutically active antidiabetic agent(s), which is/are released immediately upon oral administration of the spaced drug delivery system.

It is yet another particular object of the present invention to provide a spaced drug delivery system as referred above, wherein the first composition is a timed pulse release composition that releases as a pulse an antidiabetic agent after a predetermined time spacing or interval after oral administration of the spaced drug delivery system.

It is a further object to provide a spaced drug delivery system containing a timed pulse release composition comprising a core composition comprising one or more therapeutically active antidiabetic agents, a swelling agent, and optionally water soluble compound(s) for inducing osmosis, and a coat composition comprising one or more film forming polymers, wherein upon swelling of the core the coat ruptures and releases as a pulse the therapeutically active agent in a reliable manner at about a predetermined time after oral administration of the spaced drug delivery system.

SUMMARY OF THE INVENTION

The present invention provides a method of administration of two or more therapeutically active agents comprising orally administering to a patient a spaced drug delivery system, wherein at least one first therapeutically active agent is released immediately upon oral administration of the spaced drug delivery system, and at least one second therapeutically active agent is released as a pulse at a predetermined time after oral administration, wherein the two or more therapeutically active agents act on the disease condition by similar or dissimilar, but complementary mechanisms, to control the symptoms of the disease, or a measurable indicator of the disease condition, and further wherein the time of release of the two or more therapeutically active agents is designed to provide desired control on the disease condition.

The present invention also provides a method of administration of two or more therapeutically active agents comprising orally administering to a patient a spaced drug delivery system at a specified time prior to food intake by the patient, wherein at least one therapeutically active agent is released immediately upon oral administration of the spaced drug delivery system, and at least one therapeutically active agent is released, as a pulse, after a delay at about the time when food is taken.

Particularly, the present invention provides above referred methods of administration for two or more therapeutically active antidiabetic agents.

Further, the present invention provides a spaced drug delivery system designed to provide desired control on the disease condition, comprising
  a. a first composition comprising one or more first therapeutically active agents, and
  b. a second composition comprising one or more second therapeutically active agents,
wherein at least one first therapeutically active agent is released immediately upon oral administration of the spaced drug delivery system, and at least one second therapeutically active agent is released as a pulse at a predetermined time after oral administration, wherein the two or more therapeutic agents act on the disease condition by similar or dissimilar, but complementary mechanisms, to control the symptoms of the disease, or a measurable indicator of the disease condition, and further wherein the time of release of the two or more therapeutically active agents is designed to provide desired control on the disease condition.

The present invention, in particular, provides a spaced drug delivery system for the treatment of diabetes mellitus or conditions associated with diabetes mellitus, comprising—
  a. a first composition comprising one or more therapeutically active antidiabetic agent(s), which is/are released as a pulse after a delay, and
  b. a second composition comprising one or more therapeutically active antidiabetic agent(s), which is/are released immediately upon oral administration of the spaced drug delivery system.

Preferably, in the spaced drug delivery system as referred above, the first composition is a timed pulse release composition that releases as a pulse an antidiabetic agent after a predetermined time spacing or interval after oral administration of the spaced drug delivery system.

More particularly and specifically, the present invention provides a spaced drug delivery system containing a timed pulse release composition comprising a core composition comprising one or more therapeutically active antidiabetic agents, a swelling agent, and optionally water soluble compound(s) for inducing osmosis, and a coat composition comprising one or more film forming polymers, wherein upon swelling of the core the coat ruptures and releases as a pulse the therapeutically active agent in a reliable manner at about a predetermined time after oral administration of the composition.

As referred to herein, 'conditions associated with diabetes mellitus' include those conditions associated with the pre-diabetic state, conditions associated with diabetes mellitus itself and complications associated with diabetes mellitus. When used herein the term 'conditions associated with pre-diabetic state' includes conditions such as insulin resistance, including hereditary insulin resistance, impaired glucose tolerance, obesity and hyperinsulinaemia. 'Conditions associated with diabetes mellitus' itself include hyperglycemia, insulin resistance, including acquired insulin resistance and obesity. Further conditions associated with diabetes mellitus itself include hypertension and cardiovascular disease, especially atherosclerosis and conditions associated with insulin resistance. Conditions associated with insulin resistance include polycystic ovarian syndrome and steroid induced insulin resistance and gestational diabetes. 'Complications associated with diabetes mellitus' includes renal disease, especially renal disease associated with Type II diabetes, neuropathy and retinopathy. Renal diseases associated with Type II diabetes include nephropathy, glomerulonephritis, glomerular sclerosis, nephritic syndrome, hypertensive nephrosclerosis and end stage renal disease.

DETAILED DESCRIPTION OF THE INVENTION

The present invention provides a method of administration of two or more therapeutically active agents comprising orally administering to a patient a spaced drug delivery system, wherein at least one first therapeutically active agent is released immediately upon oral administration of the spaced drug delivery system, and at least one second therapeutically active agent is released as a pulse at a predetermined time after oral administration, wherein the two or more therapeutic agents act on the disease condition by similar or dissimilar, but complementary mechanisms, to control the symptoms of the disease, or a measurable indicator of the disease condition, and further wherein the time of release of the two or more therapeutically active agents is designed to provide desired control on the disease condition. The spaced drug delivery system can be suitably optimized to provide improved control on the disease condition when there is an easily measurable indicator of the disease condition such as blood pressure, pulse, blood glucose level, frequency of urination, ophthalmic pressure, etc. However, based on clinical observation of the symptoms of the disease coupled with the blood level profile of the therapeutically active agent, the optimization of the system can also be suitably achieved.

The therapeutically active agent may be selected from the therapeutic class viz. alcohol abuse preparations, drugs used for Alzheimer's disease, anesthetics, acromegaly agents, analgesics, antiasthmatics, anticancer agents, anticoagulants, antithrombotic agents, anticonvulsants, antidiabetics, antiemetics, antiglaucoma agents, antihistamines, anti-infective agents, antiparkinsons agents, antiplatelet agents, antirheumatic agents, antispasmodics, anticholinergic agents, antitussives, carbonic anhydrase inhibitors, cardiovascular agents, cholinesterase inhibitors, agents for the treatment of CNS disorders, CNS stimulants, cystic fibrosis management agents, dopamine receptor agonists, agents for endometriosis management, erectile dysfunction therapy, fertility agents, gastrointestinal agents, immunomodulators, immunosuppressives, memory enhancers, migraine preparations, muscle relaxants, nucleoside analogues, osteoporosis management agents, parasympathomimetics, prostaglandins, psychotherapeutic agents, sedatives, hypnotics, tranquillizers, drugs used for skin ailments, steroids and hormones.

The term "release as a pulse" refers to release characteristic of conventional tablets and capsules that are devoid of design characteristics that result in slow, extended, controlled or retarded release of the therapeutically active agent. For example, in a particular embodiment where the predetermined time of pulse release is about 70 min, the "release of therapeutically active agent as a pulse" comprises release of not more than 10% of the active ingredient at 45 min and at least 70% of the active ingredient at 2 hrs, when tested by subjecting the tablets to USP dissolution test using pH 6.8 buffer at 37±0.5° C., in a USP Type II apparatus at an rpm of 75.

The present invention also provides a method of administration of two or more therapeutically active agents comprising orally administering to a patient a spaced drug delivery system at a specified time prior to food intake by the patient, wherein at least one therapeutically active agent is released immediately upon oral administration of the spaced drug delivery system, and at least one therapeutically active agent is released as a pulse after a delay at about the time when food is taken i.e. either immediately prior to meals, or at the time of meals, or after meals.

Particularly, the present invention provides above referred methods of administration for two or more therapeutically active antidiabetic agents.

Further, the present invention provides a spaced drug delivery system designed to provide desired control on the disease condition, comprising—
   a. a first composition comprising one or more first therapeutically active agents, and
   b. a second composition comprising one or more second therapeutically active agents,
wherein at least one first therapeutically active agent is released immediately upon oral administration of the spaced drug delivery system, and at least one second therapeutically active agent is released as a pulse at a predetermined time after oral administration, wherein the two or more therapeutic agents act on the disease condition by similar or dissimilar, but complementary mechanisms, to control the symptoms of the disease, or a measurable indicator of the disease condition, and further wherein the time of release of the two or more therapeutically active agents is designed to provide desired control on the disease condition. None of the prior arts disclose such spaced drug delivery systems.

The present invention, in particular, provides a spaced drug delivery system for the treatment of diabetes mellitus or conditions associated with diabetes mellitus, comprising—
   a. a first composition comprising one or more therapeutically active antidiabetic agent(s), which is/are released as a pulse after a delay, and
   b. a second composition comprising one or more therapeutically active antidiabetic agent(s), which is/are released immediately upon oral administration of the spaced drug delivery system.

Preferably, in the spaced drug delivery system as referred above, the first composition is a timed pulse release composition that releases as a pulse an antidiabetic agent after a predetermined time spacing or interval after oral administration of the spaced drug delivery system.

More particularly and specifically, the present invention provides a spaced drug delivery system containing a timed pulse release composition comprising a core composition comprising one or more therapeutically active antidiabetic agents, a swelling agent, and optionally water soluble compound(s) for inducing osmosis, and a coat composition comprising one or more film forming polymers, wherein upon swelling of the core the coat ruptures and releases as a pulse the therapeutically active agent.

In the present invention, the total amount of active ingredient is contained in one single unit of the timed pulse release composition and is intended to be released as a pulse at the predetermined time. An important requirement for using such systems in a large number of patients is that the system should deliver the drug as a pulse at about the predetermined time in a reliable manner to the large number of patients to whom the system is administered. Thus, the coat rupture should occur reliably, the core should disintegrate immediately, and consequently the drug should be released as a pulse reliably. For instance, if in five to ten out of a hundred times the coatings do not open or rupture at about the predetermined time but rupture at a significantly prolonged time when tested by agitation over a range of agitational conditions and aqueous compositions, then the desired release at the predetermined time is not achieved reliably. Also, if the release prior to rupture or the rupture time is significantly influenced by changes in pH, composition of the surrounding fluids and the agitation conditions, then the desired release at the predetermined time is not achieved reliably. Also, if the coat rupture occurs but the therapeutically active agent is not released as a pulse in all or some of the units, then the desired release as a pulse at a predetermined time is not achieved reliably. The timed release composition in the spaced drug delivery system of the present invention has these desirable attributes such that the coat ruptures and releases as a pulse the therapeutically active agent in a reliable manner at about a predetermined time after oral administration of the composition.

Particularly, in the spaced drug delivery system of the present invention, the timed pulse release composition is optimized as follows:

a. the core composition is capable of swelling at a desired rate to a sufficient extent, b. the coat composition has the desirable film strength, plasticity, and water permeability, and c. the amount of coat composition applied is adjusted, such that upon swelling of the core the coat ruptures and releases as a pulse the therapeutically active agent in a reliable manner at about the predetermined time after oral administration of the composition, wherein the reliable manner of rupture comprises rupturing of 36 tablets out of a total of 36 tablets at about the predetermined time, when tested by subjecting the tablets to USP dissolution test using an aqueous media at 37±0.5° C., in a USP Type I or Type II apparatus at an rpm selected from the range of about 50 rpm to about 100 rpm. Further wherein the predetermined time is in the range of about 1 hr to about 4 hr, the 36 out of the 36 tablets rupture within ±50% of the predetermined time; and wherein the predetermined time is in the range of about >4 hr to about 12 hr, the 36 out of the 36 tablets rupture within ±25% of the predetermined time.

In specific preferred embodiments, the spaced drug delivery system of the present invention includes—

1. A spaced drug delivery system wherein the antidiabetic agent in the first composition is a biguanide antidiabetic agent, and the antidiabetic agent in the second composition is a sulfonyl urea.

2. A spaced drug delivery system wherein the antidiabetic agents in the first composition are selected from the group consisting of an alpha glucosidase inhibitor, a thiazolidinedione, and an insulin secretagogue; and the antidiabetic agent in the second composition is an insulin secretagogue; further wherein the insulin secretagogues, if present in both first and second compositions, are not the same.

3. A spaced drug delivery system wherein the antidiabetic agent in the first composition is a biguanide antidiabetic agent, and the antidiabetic agent in the second composition is selected from the group consisting of insulin secretagogue and a thiazolidinedione, optionally in combination with an alpha glucosidase inhibitor.

4. A spaced drug delivery system wherein the antidiabetic agent in the first composition is a biguanide antidiabetic agent, and the antidiabetic agent in the second composition is an alpha glucosidase inhibitor.

In the present invention, the timed pulse release composition imbibes fluids from the environment of use causing the swelling agent in the core to swell. The therapeutically active antidiabetic agent is then released after the timed pulse release coat ruptures under the influence of mechanical pressure exerted by the swelling of the swelling agent(s) present in the core. The time of rupture of the coat can be controlled by varying (a) the degree and rate of swelling of the core; (b) the timed pulse release coat composition, by using different components and ratios of these components; and (c) the thickness of the coat.

The swelling agent used in the timed pulse release composition includes one or more swellable hydrophilic polymers. The quantity or relative proportion of the polymers is subject to considerable variation. However, a sufficient quantity of the material is present in the core to provide, upon uptake of water, a swelling pressure in excess of the cohesive strength of the coating surrounding the tablet or core. Preferably, the polymers are employed in the dry state or in a form that has substantial capacity for water uptake. Examples of swellable hydrophilic polymers that may be used in the timed pulse release composition of the present invention as the swelling agent include vinylpyrrolidone polymers such as povidone, or crosslinked polyvinylpyrrolidone such as crospovidone; cellulose and cellulose derivatives such as microcrystalline cellulose, methylcellulose, ethylcellulose, hydroxypropylcellulose, hydroxypropyl methylcellulose, carboxyalkyl celluloses or crosslinked carboxyalkylcelluloses and their alkali salts; sodium starch glycolate, starch and starch derivatives, ion-exchange resins and mixtures thereof. Preferably, the swelling agent used comprises a swelling agent that swells considerably but does not form a strong gel and may be selected from the group consisting of crosslinked sodium carboxymethyl cellulose, crosslinked polyvinylpyrrolidone and sodium starch glycolate. The preferred swelling agents also have a strong wicking action and are capable of swelling to several times their original volume on imbibing water from the surroundings.

The alkali salt of crosslinked carboxyalkyl cellulose, i.e. crosslinked sodium carboxymethyl cellulose, also known as croscarmellose sodium or Ac-Di-Sol, is available commercially as Nymcel® ZSX, Pharmacel® XL, Primellose® or Solutab®. The amount of swelling agent that may be used is dependent on the desired time of rupture of the timed pulse release coat, nature and amounts of other components in the core, as well as the composition and thickness of the coat. Generally, croscarmellose sodium may be used as the polymeric swelling agent, in an amount ranging from about 0.5% to about 50% by weight of the core, preferably from about 2% to about 40% by weight of the core, more preferably from about 5% to about 20% by weight of the core. In specific preferred embodiments croscarmellose sodium is used in a range from about 6% to about 10% by weight of the core, more preferably from about 7% to about 9% by weight of the core.

Vinyl pyrrolidone polymers or polyvinyl pyrrolidone (PVP), also referred to as Povidone, are synthetic polymers consisting essentially of linear 1-vinyl-2-pyrrolidinone groups, the degree of polymerization of which results in polymers of various molecular weights, the molecular weight ranging between 2500 and 3,000,000 Daltons. PVP is commercially available as Kollidon® (BASF), Plasdone® and Peristone® (General Aniline). PVP is classified into different grades on the basis of its viscosity in aqueous solution. Different grades of PVP available are PVP K-12, PVP K-15, PVP K-17, PVP K-25, PVP K-30, PVP K-60, PVP K-90 and PVP K-120. The K-value referred to in the above nomenclature is calculated from the viscosity of the PVP in aqueous solution, relative to that of water. Crospovidone or cross-PVP, the synthetic crosslinked homopolymer of N-vinyl-2-pyrrolidinone, may also be used as a swellable hydrophilic polymer. It is commercially available as Kollidon CL and Polyplasdone XL, and has a molecular weight higher than 1,000,000 Daltons. Crospovidone is used in the present invention in an amount ranging from about 2% to about 5% by weight of the core. The preferred vinyl pyrrolidone polymer for use as a swellable hydrophilic polymer is PVP K-30, having an approximate molecular weight of 50,000 Daltons. It may be used in an amount ranging from about 0.5% to about 5% by weight of the core, more preferably from about 1% to about 2% by weight of the core.

Sodium starch glycolate, the sodium salt of carboxymethyl ether of starch, may also be used as the polymeric swelling agent. It has a molecular weight ranging between 500,000 and 1,000,000 Daltons, and is commercially available as Explotab and Primojel. Sodium starch glycolate may be used in the present invention in an amount ranging from about 0.5% to about 40% by weight of the core, preferably from about 2% to about 40% by weight of the core, more preferably from about 2% to about 10% by weight of the core.

Preferably, the timed pulse release composition in the spaced drug delivery system of the present invention contains a wicking agent. The term wicking agent as used herein implies a broader definition than a conventional wicking agent and includes any pharmaceutical excipient that provides influx of water into the core by any suitable mechanism, preferably by capillary action as is typical of conventional wicking agents. Materials suitable for use as wicking agents in the timed pulse release composition include, but are not limited to, colloidal silicon dioxide, kaolin, titanium dioxide, fumed silicon dioxide, alumina, sodium lauryl sulfate, microcrystalline cellulose, low molecular weight polyvinyl pyrrolidone, bentonite, magnesium aluminum silicate, and the like.

Microcrystalline cellulose (MCC) is used in the preferred embodiment as the wicking agent. It is made up of a chain of about 250 glucose molecules in the form of a microcrystal, consisting primarily of crystallite aggregates obtained by removing amorphous regions of a pure cellulose source material by hydrolytic degradation using mineral acid. MCC has an average molecular weight of about 36,000 Daltons and is available in various grades, which differ in bulk density, particle size and moisture content. It is commercially available as Vivapur®, Avicel®, Vivacel®, Emcocel®, Fibrocel® and Tabulose®. Avicel® PH 102, having a mean particle size of 100 µm, i.e. 8% or less of the particles are retained on a # 60 sieve (as defined by ASTM, American Society for Testing and Materials), and 45% or more of the particles are retained on a #200 sieve (as defined by ASTM), and having a moisture content ≦5%, is used in more preferred embodiments of the timed pulse release composition, in an amount ranging from about 2% to about 5% by weight of the core, more preferably from about 2% to about 3% by weight of the core.

Water-soluble compounds suitable for inducing osmosis, i.e. osmotic agents or osmogents, are generally used in the core of the timed pulse release composition when the drug itself does not exert sufficient osmotic pressure in order to imbibe fluid from the surroundings. Osmogents that may be present in the core of the timed pulse release composition include all pharmaceutically acceptable and pharmacologically inert water-soluble compounds referred to in the pharmacopoeias such as United States Pharmacopoeia, as well as in Remington: The Science and Practice of Pharmacy, edition 20, Lippincott Williams and Wilkins, Philadelphia. (2000). Pharmaceutically acceptable water-soluble salts of inorganic or organic acids, or non-ionic organic compounds with high water solubility, e.g. carbohydrates such as sugar, or amino acids, are generally preferred. The examples of agents used for inducing osmosis include inorganic salts such as magnesium chloride or magnesium sulfate, lithium, sodium or potassium chloride, lithium, sodium or potassium hydrogen phosphate, lithium, sodium or potassium dihydrogen phosphate, salts of organic acids such as sodium or potassium acetate, magnesium succinate, sodium benzoate, sodium citrate or sodium ascorbate; carbohydrates such as mannitol, sorbitol, arabinose, ribose, xylose, glucose, fructose, mannose, galactose, sucrose, maltose, lactose, raffinose; water-soluble amino acids such as glycine, leucine, alanine, or methionine; urea and the like, and mixtures thereof. The amount of osmogents that may be used depends on the particular osmogent that is used and may range from about 1% to about 60% by weight of the core.

In addition to the above ingredients, the core of the timed pulse release composition may optionally contain pharmaceutically acceptable excipients such as binders, disintegrants, lubricants and the like. Examples of binders used commonly include starch, gelatin, sugars like sucrose, glucose, dextrose, molasses and lactose; acacia, sodium alginate, cellulose derivatives like methyl cellulose, ethyl cellulose, carboxymethyl cellulose and the like; polymers such as polyvinyl pyrrolidone, Veegum, polyethylene glycol, waxes and the like. The timed pulse release composition of the present invention may be optimized to obtain the reliable manner of rupture without the use of a wicking agent. However, the use of a wicking agent has been found to be useful in that the task of optimization to obtain the reliable manner of rupture is made easier.

Examples of lubricants that may be used in the timed pulse release composition include talc, magnesium stearate, calcium stearate, aluminium stearate, stearic acid, hydrogenated vegetable oils, colloidal silicon dioxide, polyethylene glycol, cellulose derivatives such as carboxyalkyl cellulose and its alkali salts, or mixtures thereof. Hydrophobic or water insoluble lubricants may reduce the water imbibing properties of the core whereas hydrophilic or water soluble lubricants do not, and are preferable. A more preferred lubricant is colloidal silicon dioxide. A mixture of colloidal silicon dioxide and magnesium stearate may be used as the preferred lubricant. More preferred embodiments use a combination of microcrystalline cellulose and colloidal silicon dioxide as the wicking agents, with colloidal silicon dioxide also functioning as a lubricant. Colloidal silicon dioxide is available commercially as Aerosil® from Degussa-Huls, Nippon and Fischer GmbH. The preferred colloidal silicon dioxide lubricant is Aerosil® 200, with an approximate external surface area of 200 $m^2/g$. The colloidal silica may be used in amounts in the range of about 0.5% to about 5% by weight of the core.

In a preferred embodiment, the core of the timed pulse release composition is obtained by mixing the therapeutically active agent and the swelling agent with the binder in a rapid mixer granulator and granulating the mixture. In more preferred embodiments of the present invention, only a part of the total swelling agent is included in the composition and the remaining is mixed at the lubrication stage with the dried granules. The granules obtained using a suitable granulating solvent are wet milled through a screen and then dried in a fluidised bed drier at 40-50° C. to a moisture content of 2-3%. The dried granules are then milled through a 2 mm screen and are mixed with one or more lubricants and the wicking agent. In more preferred embodiments, as described above, the remaining part of the swelling agent is mixed at this stage.

The lubricated granules may be filled in hard gelatin capsules, or may be compressed to obtain the compressed tablets or cores.

The therapeutically active agent comprising compressed cores/capsules are covered with a coat composition comprising one or more film forming polymers, to provide a timed pulse release composition. The film forming polymers that may be used to form this timed pulse release composition are selected from the group consisting of water insoluble polymers, pH dependent polymers, and mixture of water soluble and water insoluble polymers, or mixtures thereof. Examples of film forming polymers that may be used include cellulose ester derivatives like methyl cellulose, ethyl cellulose, hydroxypropyl cellulose, hydroxypropyl methylcellulose, cellulose acetate, cellulose acetate phthalate, pH-independent copolymers of methacrylic acid and methacrylic acid esters commercially available as Eudragit®, or mixtures thereof. The time of release of the therapeutically active agent of the first composition may be varied by varying the components used to form the coat, and/or by varying the ratio in which these components are used. By selecting the suitable components and by using them in suitable ratios, the release can be obtained at about a predetermined time after oral administration of the spaced drug delivery system. A preferred embodiment of the invention uses a mixture of a water-insoluble polymer and a water soluble polymer to form the delayed release coat. In preferred embodiments ethyl cellulose is used as the water-insoluble polymer and hydroxypropyl methylcellulose (HPMC) is used as the water soluble polymer. The mixture is used in a preferred weight ratio of 0:20 to 20:0 of ethyl cellulose : HPMC, more preferably 6:3 to 9:3.

The compressed cores/capsules containing the therapeutically active agent are coated with the coating solution, comprising the film forming polymers in a suitable solvent system, to a defined weight gain, the thickness of the coat depending on the predetermined time of release of the active agent. The coating material may be applied by any procedure which provides a continuous film of essentially uniform thickness. One method of coating involves rotating a bed of uncoated cores in a conventional tablet coating pan and applying a solution or dispersion of the coating agent in a suitable solvent by pouring or spraying the solution onto the moving cores. Other coating procedures such as fluid bed coating, vertical spray coating, and the like can also be employed. The coated cores are dried by exposing them to warm, dry air and may be cured, if necessary, by air drying, baking or force drying. In one embodiment of the present invention, the compressed core is coated with a ethyl cellulose:HPMC solution to a weight gain in the range of about 2% to about 20% by weight of the compressed core, preferably from about 5% to about 10% by weight of the core; more preferably from about 9% to about 10% by weight of the compressed core. The cores are coated in an automated perforated coating pan followed by drying and curing of the coated cores in a tray drier for 24 hours at 40-50° C.

The present invention covers any spaced drug delivery system in which the first composition comprising the therapeutically active antidiabetic agent, and the second composition comprising the therapeutically active antidiabetic agent, are physically separated, or compartmentalized, so as to achieve different release rates of the two active agents. Such separation, or compartmentalization, may be on a macroscale, for instance, with the agents being incorporated into separate units (such as tablets, powder, granules, pellets etc) for simultaneous or sequential administration, or separation of the agents may be on a micro-scale, for instance, with the agents being present within the same unit. Two separate units when present are formed into a single unit spaced drug delivery system by filling them into capsules.

In the spaced drug delivery system of the present invention, the first and second composition may be in the form of either multiparticulates such as particles, pellets or granules, or present as concentric or laminar tablet layers or as single units such as a compressed tablet. The multiparticulates may be made by any of the conventional methods, including mixing, granulation, extrusion, spheronisation, layering of non-pareil seeds, etc, and various other methods known to a person skilled in the art. A compressed tablet core may be obtained by compressing the multiparticulates in a tablet die. The first composition is surrounded by a delayed release coating comprising delayed release material selected from the group consisting of enteric polymers, water insoluble polymers, hydrophobic compounds, hydrophilic non-polymeric compounds, hydrophilic polymers and the like, and mixtures thereof, using conventional coating methods. The coated multiparticulates or tablets of the first composition and the uncoated multiparticulates or tablets of the second composition, may be filled into capsules. Alternatively, tablets of the first composition may be surrounded by the second composition and compressed in a compression coating tablet machine or a second layer of the second composition may be compressed onto the compressed first composition to form bilayer tablets.

The second composition used in the spaced drug delivery system is in the form of multiparticulates or tablets, which may be filled into capsules along with the first timed pulse release composition. Alternatively, tablets of the first timed pulse release composition may be surrounded by the second composition and compressed in a compression coating tablet machine to obtain a single unit dose form with timed pulse release core composition and an immediate release coat composition comprising the therapeutically active agent of the second composition. The second composition may be included in the spaced drug delivery system of the present invention in different ways. Multiparticulates of the therapeutically active agent of the second composition may be obtained by mixing the agent with pharmaceutically acceptable excipients, such as binders, fillers, disintegrants and the like, or by further granulating the mixture. The granules so obtained are dried and lubricated with one or more lubricants.

The immediate release layer of the second composition may be introduced by mixing the therapeutically active antidiabetic agent with pharmaceutical adjuvants such as film-forming agents, plasticisers and the like, in a suitable solvent or solvent system, and coating the timed pulse release composition, using conventional coating methods known to a person skilled in the art. Examples of film-forming agents that may be used in the present invention include cellulose derivatives such as cellulose acetate phthalate, hydroxypropyl methylcellulose, hydroxypropyl cellulose, hydroxypropyl ethylcellulose, ethyl cellulose, methyl cellulose, microcrystalline cellulose, methacrylic acid/methacrylate esters, polyvinyl acetate phthalate, shellac and the like, or mixtures thereof. Hydroxypropyl methylcellulose (HPMC) is used as the preferred film-forming agent along with the therapeutically active agent in the present invention, in an amount ranging from about 2% to about 20% by weight of the timed pulse release composition, more preferably from about 2% to about 5% by weight of the composition. Examples of plasticisers that may be used in the present invention include, but are not limited to glycerol, propylene glycol, polyethylene glycol, sorbitol, triacetin, diethyl phthalate, mineral oil, petrolatum, lanolin and the like. In a preferred embodiment of the present invention, polyethylene glycol (PEG) 4000 is used as the plasticiser in an amount ranging from 0% to about 5% by weight of the core, more preferably from about 0.1% to about 1% by weight of the core. The therapeutically active agent, HPMC and PEG 4000 are mixed in a suitable solvent or solvent system. The solution thus obtained is used to coat the core of the timed pulse release composition to a desired weight gain, in a conventional tablet coating pan. The tablets are then dried in a tray drier at a temperature of 40-50° C. for 24 hours.

The spaced drug delivery system is designed to allow immediate release of at least one therapeutically active antidiabetic agent and a delayed release of at least one therapeutically active antidiabetic agent.

The present invention is further described with reference to a specific embodiment wherein one antidiabetic agent that is released immediately upon oral administration is a biguanide antidiabetic agent and one antidiabetic agent that is release as a pulse after a predetermined time after administration is a sulfonyl urea; however this is meant only for the purpose of illustration and is by no means intended to limit the spirit and scope of the present invention.

Examples of biguanide antidiabetic agents that may be used in the present invention include metformin, phenformin and buformin, and their pharmaceutically acceptable salts.

Examples of sulfonyl ureas that may be used in the present invention include acetohexamide, carbutamide, chlorpropamide, glipizide, glyburide (glibenclamide), glimepiride, gliclazide, glibornuride, gliquidone, glisoxepid, glyhexamide, phenbutamide, tolazamide, tolbutamide, tolcyclamide, and the like.

The amounts of the biguanide antidiabetic agent and the sulfonyl urea are selected such that the combination provides optimum benefits in cases of diabetes mellitus or conditions associated with diabetes mellitus, while reducing the untoward effects. The RE 37330 patent claims use of a combination of glibenclamide and metformin in a method of treating non-insulin dependent diabetes mellitus, in a ratio of 1:100. The results of the clinical study mentioned in the RE 37330 patent indicate that a maximum daily dose of sulfonyl urea considered optimum for the most severe, barely controllable cases is 15 mg. However, such a dose has to be combined with a biguanide maximum daily dose of 1500 mg in order to obtain the maximum therapeutical effect together with the reduction of untoward effects. The patent claims use of the combination in other ratios such as those having a weight ratio of 1:160 to 1:200.

In preferred embodiments, the sulfonyl urea used in the second composition is glipizide. In yet another preferred embodiment, the sulfonyl urea of the second composition is glibenclamide. Metformin, or its pharmaceutically acceptable salt, preferably the hydrochloride salt, is used as the preferred biguanide antidiabetic agent in the present invention. The metformin hydrochloride and glipizide are preferably used in a metformin hydrochloride to glipizide weight ratio ranging from about 250:1 to about 50:1. Glipizide is used in an amount ranging from about 2 mg to about 15 mg, while metformin hydrochloride is used in an amount ranging from about 200 mg to about 1.5 gm. For instance, the unit spaced drug delivery system comprises 250 mg metformin hydrochloride and 2.5 mg glipizide, or 850 mg metformin hydrochloride and 5 mg glipizide, or 1 g metformin hydrochloride and 10 mg glipizide. In preferred embodiments the unit spaced drug delivery system comprises 500 mg metformin hydrochloride and 5 mg glipizide. The metformin hydrochloride-glibenclamide combination is used in a metformin hydrochloride to glibenclamide weight ratio ranging from about 250:1 to about 50:1, more preferably in a ratio of 100:1. Glibenclamide is used in an amount ranging from about 1 mg to about 10 mg, while metformin hydrochloride is used in an amount ranging from about 200 mg to about 1.5 gm. In preferred embodiments the unit spaced drug delivery system comprises 250 mg metformin hydrochloride and 1.25 mg glibenclamide, or 5000 mg metformin hydrochloride and 2.5 mg glibenclamide, more preferably 250 mg metformin hydrochloride and 2.5 mg glibenclamide, still more preferably 500 mg metformin hydrochloride and 5 mg glibenclamide.

The following examples do not limit the scope of the invention and are presented as illustrations.

EXAMPLE 1

The spaced drug delivery system of the present invention is obtained as mentioned in Table 1 below.

TABLE 1

| Ingredients | Quantity (mg) | Percent % w/w. |
|---|---|---|
| A. Immediate release sulfonyl urea granules - | | |
| Glipizide | 5.0 | 6.67 |
| Microcrystalline cellulose (MCC) | 13.0 | 17.33 |
| Lactose monohydrate | 51.175 | 68.23 |
| Polyvinyl pyrrolidone (PVP K-30) | 1.5 | 2.0 |
| Sodium starch glycolate | 3.5 | 4.67 |
| Sodium lauryl sulfate | 0.075 | 0.1 |
| Magnesium stearate | 0.75 | 1.0 |
| Total | 75 | 100.0 |
| B. Delayed release biguanide core - Core - | | |
| Metformin hydrochloride | 500.0 | 83.33 |
| Croscarmellose sodium (Ac-Di-Sol) | 50.0 | 8.33 |
| Corn starch, plain (as 10% starch paste) | 17.0 | 2.83 |
| Microcrystalline cellulose (MCC) | 13.5 | 2.25 |
| Colloidal silicon dioxide | 13.5 | 2.25 |
| Magnesium stearate | 6.0 | 1.0 |
| Total | 600.0 | 100.0 |
| Coat - | | |
| Ethyl cellulose | 40.7 | coated to a weight gain of 9.5% by weight of the core. |
| Hydroxypropyl methylcellulose | 16.3 | |

The immediate release sulfonyl urea granules were obtained by sifting glipizide, lactose monohydrate and microcrystalline cellulose (MCC) and sodium starch glycolate through a # 40 sieve (as defined by American Society for Testing and Materials, ASTM) and blending the powders suitably. A solution of PVP K-30 in water was used to granulate the dry powder blend. The granules thus obtained were dried to a moisture content of not more than 3%. These granules were then passed through a # 25 sieve (as defined by ASTM). The granules were finally mixed with talc and magnesium stearate to obtain the final granules. The method of preparation of the delayed release biguanide core included sifting the metformin hydrochloride and croscarmellose sodium through a suitable sieve and mixing them in a rapid mixer granulator. The dry powder blend was then granulated using 10% starch paste, followed by wet milling the wet mass through a Fitz mill. The granules so obtained were dried to a moisture content of 3-4%. The dry granules are then milled in a Fitz mill through a 1.5 mm screen, followed by sifting of the granules through a # 16 sieve (as defined by ASTM). These granules of metformin hydrochloride were then mixed with MCC, colloidal silicon dioxide and magnesium stearate, and the lubricated mixture thus obtained was compressed on a rotary compression machine using oblong shaped punches. The tablets were then coated in a conventional coating pan using a solution of ethyl cellulose and HPMC in a mixture of methanol and dichloromethane.

The delayed release biguanide core was then mixed with 75 mg of the immediate release sulfonyl urea granules and encapsulated in a size '0' hard gelatin capsule. The delayed release biguanide composition and 75 mg of sulfonyl urea granules were subjected to dissolution studies using pH 6.8 buffer at 37±0.5° C., in a USP Type II apparatus (rpm=75). The release profile for metformin is recorded in Table 2 below, while that for glipizide is recorded in Table 3 below. The rupture time of the timed pulse release coating on the biguanide core was observed for 30 tablets, which were subjected to dissolution testing. It was found that all the tablets opened reliably at about 1 hour to about 1.3 hour after start of the dissolution test.

TABLE 2

| Time (mins) | % metformin released (±S.D.) |
| --- | --- |
| 45 | 1 ± 0.5 |
| 105 | 91 ± 6.89 |
| 120 | 98 ± 4.26 |

TABLE 3

| Time (min) | % glipizide released (±S.D.) |
| --- | --- |
| 45 | 88 ± 2.19 |

The tablets were tested in different media, using different conditions of pH and apparatus, and the opening time was recorded. The observations are recorded in Table 4 below.

TABLE 4

| No. | Medium used | Conditions used | Opening time of 6 tablets (hours · min) |
| --- | --- | --- | --- |
| 1. | pH 6.8 | USP Type I apparatus, rpm of 100 | 1.08, 1.25, 1.13, 1.16, 1.02, 1.12 |
| 2. | pH 6.8 | USP Type I apparatus, rpm of 100 | 1.04, 1.14, 1.18, 1.09, 1.09, 1.25 |
| 3. | pH 6.8 | USP Type I apparatus, rpm of 100 | 1.23, 1.05, 0.59, 1.12, 0.58, 1.25 |
| 4. | pH 6.8 | USP Type I apparatus, rpm of 100 | 1.18, 1.26, 1.24, 1.01, 1.12, 1.06 |
| 5. | pH 6.8 | USP Type II apparatus, rpm of 75 | 1.28, 1.30, 1.21, 1.17, 1.09, 1.03 |
| 6. | 0.1N HCl | USP Type II apparatus, rpm of 75 | 1.07, 1.18, 1.21, 1.10, 1.03, 1.30 |
| 7. | pH 6.8 | USP Type II apparatus, rpm of 50 | 1.02, 1.39, 1.28, 1.21, 1.03, 1.26 |
| 8. | 0.1N HCl | USP Type II apparatus, rpm of 50 | 1.24, 1.10, 1.05, 1.12, 1.29, 0.50 |

EXAMPLE 2

The spaced drug delivery system of the present invention is obtained as mentioned in Table 5 below.

TABLE 5

| Ingredients | Quantity (mg) | Percent % w/w. |
| --- | --- | --- |
| A. Immediate release sulfonyl urea granules - | | |
| Glipizide | 5.0 | 6.67 |
| Lactose monohydrate | 64.175 | 85.56 |
| Sodium starch glycolate | 3.5 | 4.67 |
| Polyvinyl pyrrolidone (PVP K-30) | 1.5 | 2.0 |
| Sodium lauryl sulfate (SLS) | 0.075 | 0.1 |
| Magnesium stearate | 0.75 | 1.0 |
| Total | 75 | 100.0 |
| B. Delayed release biguanide core - Core - | | |
| Metformin hydrochloride | 500.0 | 83.33 |
| Croscarmellose sodium (Ac-Di-Sol) | 50.0 | 8.33 |

TABLE 5-continued

| Ingredients | Quantity (mg) | Percent % w/w. |
|---|---|---|
| Corn starch, plain (as 10% starch paste) | 17.0 | 2.83 |
| Microcrystalline cellulose (MCC) | 13.5 | 2.25 |
| Colloidal silicon dioxide | 13.5 | 2.25 |
| Magnesium stearate | 6.0 | 1.0 |
| Total | 600.0 | 100.0 |
| Coat - | | |
| Ethyl cellulose | 42.0 | coated to a weight gain of 9.8% by weight of the core. |
| Hydroxypropyl methylcellulose | 16.8 | |

The immediate release sulfonyl urea granules were obtained by sifting glipizide, lactose monohydrate and MCC through a # 40 sieve (as defined by American Society for Testing and Materials, ASTM) and blending the powders suitably. A solution of PVP K-30 and SLS in water was used to granulate the dry powder blend. The rest of the procedure remains the same as for Example 1 above. The delayed release biguanide cores were also prepared as per the method given in Example 1 above.

The immediate release sulfonyl urea granules (75 mg) were mixed with the delayed release biguanide core and the mixture was encapsulated. The delayed release biguanide composition and the sulfonyl urea granules were subjected to dissolution studies using pH 6.8 buffer at 37±0.5° C., in a USP Type II apparatus (rpm=75). The release profile for metformin is recorded in Table 6 below, while that for glipizide is recorded in Table 7 below. The rupture time for timed pulse release coating on the biguanide core was observed for 30 tablets, which were subjected to dissolution testing. It was found that all tablets opened reliably at about 1 hour to about 1.3 hour after start of the dissolution test.

TABLE 6

| Time (min) | % metformin released |
|---|---|
| 45 | 1 |
| 120 | 91 ± 5.33 |

TABLE 7

| Time (min) | % glipizide released |
|---|---|
| 45 | 98 ± 1.55 |

The tablets obtained as per example 2 of the present invention were tested in water, using different conditions of pH apparatus, and the opening time was recorded. The observations are recorded in Table 8 below.

TABLE 8

| No. | Medium | Conditions used | Opening time of 6 tablets (hours · min) |
|---|---|---|---|
| 1. | pH 6.8 | USP Type I apparatus, with rpm of 100 | 1.15, 1.04, 1.16, 1.13, 1.21, 1.16 |
| 2. | pH 6.8 | USP Type I apparatus, with rpm of 100 | 1.37, 1.18, 1.20, 1.12, 1.00, 1.15 |
| 3. | pH 6.8 | USP Type I apparatus, with rpm of 100 | 1.02, 1.15, 1.07, 1.10, 1.15, 0.53 |
| 4. | 0.1N HCl | USP Type II apparatus, with rpm of 75 | 1.11, 1.10, 0.50, 0.58, 0.59, 0.45 |
| 5. | pH 6.8 | USP Type II apparatus, with rpm of 50 | 1.00, 1.09, 0.55, 1.09, 1.09, 1.22 |
| 6. | 0.1N HCl | USP Type I apparatus, with rpm of 100 | 1.02, 1.00, 1.23, 1.23, 1.26, 1.01 |

EXAMPLE 3

The spaced drug delivery system of the present invention is obtained as mentioned in Table 9 below.

TABLE 9

| Ingredients | Quantity (mg) | Percent % w/w. |
|---|---|---|
| A. Immediate release sulfonyl urea granules - | | |
| Glibenclamide | 5.0 | 6.67 |
| Lactose monohydrate | 64.175 | 85.48 |
| Sodium starch glycolate | 3.5 | 4.67 |
| Polyvinyl pyrrolidone (PVP K-30) | 1.5 | 2.0 |

TABLE 9-continued

| Ingredients | Quantity (mg) | Percent % w/w. |
|---|---|---|
| Sodium lauryl sulfate (SLS) | 0.075 | 0.1 |
| Magnesium stearate | 0.75 | 1.0 |
| Total | 75 | 100.0 |
| B. Delayed release biguanide core - Core - | | |
| Metformin hydrochloride | 500.0 | 83.33 |
| Croscarmellose sodium (Ac-Di-Sol) | 50.0 | 8.33 |
| Corn starch, plain (as 10% starch paste) | 17.0 | 2.83 |
| Microcrystalline cellulose (MCC) | 13.5 | 2.25 |
| Colloidal silicon dioxide | 13.5 | 2.25 |
| Magnesium stearate | 6.0 | 1.0 |
| Total | 600.0 | 100.0 |
| Coat - | | |
| Ethyl cellulose | 42.0 | coated to a weight gain of 9.8% by weight of the core. |
| Hydroxypropyl methylcellulose | 16.8 | |

The spaced drug delivery system was prepared by a procedure similar to Example 2. The immediate release sulfonyl urea granules (75 mg) were mixed with the delayed release biguanide core and the mixture was encapsulated.

The delayed release biguanide composition and the sulfonyl urea granules were subjected to dissolution studies. The release profile for metformin is similar to that obtained in Example 2 above. The dissolution studies for glibenclamide were carried out using 0.025M tris buffer pH 9.01 at 37±0.5° C., in a USP Type II apparatus (rpm=50) and is recorded in Table 10 below.

TABLE 10

| Time min | % glibenclamide released |
|---|---|
| 15 | 93 ± 2.09 |
| 30 | 95 ± 1.72 |
| 45 | 96 ± 1.53 |

EXAMPLE 4

The spaced drug delivery system of the present invention is obtained as mentioned in Table 11 below.

TABLE 11

| Ingredients | Quantity (mg) | Percent (%) w/w. |
|---|---|---|
| A. Immediate release granules - | | |
| Rosiglitazone maleate (equivalent to 8 mg of rosiglitazone base) | 10.6 | 11.04 |
| Lactose monohydrate | 78.09 | 81.25 |
| Sodium starch glycolate | 4.5 | 4.69 |
| PVP K-30 | 1.92 | 2.0 |
| Magnesium stearate | 0.96 | 1.0 |
| Total | 95.98 | 99.98 |

TABLE 11-continued

| Ingredients | Quantity (mg) | Percent (%) w/w. |
|---|---|---|
| B. Delayed release biguanide core - Core - | | |
| Metformin hydrochloride | 500.0 | 83.33 |
| Croscarmellose sodium (Ac-Di-Sol) | 50.0 | 8.33 |
| Corn starch, plain (as 10% starch paste) | 17.0 | 2.83 |
| Microcrystalline cellulose (MCC) | 13.5 | 2.25 |
| Colloidal silicon dioxide | 13.5 | 2.25 |
| Magnesium stearate | 6.0 | 1.0 |
| Total | 600.0 | 100.0 |
| Coat - | | |
| Ethyl cellulose | 42.0 | coated to a weight gain of 9.8% by weight of the core. |
| Hydroxypropyl methylcellulose | 16.8 | |

The spaced drug delivery system was prepared by a procedure similar to Example 2. The immediate release rosiglitazone maleate granules were mixed with the delayed release biguanide core and the mixture was encapsulated.

The delayed release biguanide composition and the rosiglitazone maleate granules were subjected to dissolution studies. The release profile for metformin is similar to that obtained in Example 2 above. The dissolution studies for rosiglitazone maleate were carried out using 0.1N HCl at 37±0.5° C., in a USP Type II apparatus (rpm=50) and are recorded in Table 12 below.

TABLE 12

| Time (min) | % rosiglitazone released |
|---|---|
| 10 | 97 ± 2.72 |
| 20 | 96 ± 3.00 |
| 30 | 96 ± 2.82 |

EXAMPLE 5

The delayed release biguanide core of the present invention was subjected to radiological studies to determine the coat rupture time in vivo. The compositions of Example 2 with the addition of 25 mg barium sulfate in the core, was used for the radiological studies. The delayed release metformin tablet cores containing barium sulfate were prepared as per the method given in Example 1 above, with the barium sulfate being mixed with the starch paste to ensure its uniform distribution in the core.

A single dose, open label study was carried out using six healthy male volunteers. The subjects were fasted overnight before dosing and for 4 hours thereafter. Drinking water was prohibited for 2 hours before dosing and 2 hours thereafter. A single barium sulfate containing delayed release metformin tablet core was administered to each volunteer as the test product along with 240 ml of drinking water. Standard meals were provided at 4 hours after dosing. X-rays were taken at the following time points after dosing: 30, 45, 60, 75 and 90 minutes. The result of the radiological follow-up at the above-mentioned time intervals is given in Table 13 below.

TABLE 13

| Vol. No. | Position of the tablet (minutes) | | | | |
|---|---|---|---|---|---|
| | 30 | 45 | 60 | 75 | 90 |
| 1 | Proximal small bowel (intact) | Proximal small bowel (intact) | Obscure (intact) | Left hyponchondrion of colon (intact) | Disappeared completely |
| 2 | Not observed | Not observed | Not observed | Not observed | Not observed |
| 3 | Small bowel (intact) | Small bowel (intact) | Obscure | Small bowel (intact) | Disappeared completely |
| 4 | Stomach fundus (intact) | Pyloric antrum (intact) | Pyloric antrum (intact) | Pyloric antrum (intact) | Proximal jejunal loop (Disintegrating) |
| 5 | Distal jejunal loop (intact) | Proximal ileal loop (intact) | Ileal loop (Disintegrating) | Ileal loop (Disintegrating) | Disappeared completely |
| 6 | Pyloric antrum (intact) | Pyloric antrum (intact) | Duodenojejunal flexure (intact) | Distal duodenum (disintegrating) | Disappeared completely | as seen in Table 13 above, the tablet was not observed in volunteer no. 2, perhaps due to insufficient barium sulfate in the core. In four of the five remaining volunteers, the tablet was completely disintegrated in 90 minutes, and in volunteer no. 4 the tablet started disintegrating at 90 minutes.

EXAMPLE 6

Comparative Example 1

This example illustrates the process of optimization of the composition to obtain, at about the predetermined time, a reliable manner of coat rupture.

Tablet cores were prepared according to the composition given in Table 14. The target coat rupture time was 1 hr.

TABLE 14

| Ingredients | Quantity (mg) |
|---|---|
| Metformin hydrochloride | 500.0 |
| Croscarmellose sodium (Ac-Di-Sol) | 34.5 |
| PVP K-90F | 10.0 |
| Magnesium stearate | 5.5 |
| Total | 550.0 |

The above cores were coated with a combination of ethylcellulose and hydroxypropyl methylcellulose dissolved in methylene chloride : methanol (4:1) solvent system. The ratio of ethylcellulose to hydroxypropyl methylcellulose was varied to evaluate its effect on the coat rupture time. When the ratio was 9:2 and the gain in weight upon coating was 4% by weight of the total weight of the core, the coat rupture time was about 2 hours. The coat rupture time could be decreased by decreasing the amount of coat applied. However, at a ethylcellulose to hydroxypropyl methylcellulose ratio of 9:2, the coat rupture time was sensitive to this factor and this could lead to coat rupture time changing with variations in amount of coat applied from batch to batch. It was found that by a small change from 4% to 3% weight gain upon coating the coat rupture time decreased to 45-60 minutes. Increase in proportion of hydroxypropyl methylcellulose decreased the coat rupture time. Ratio of ethylcellulose to hydroxypropyl methylcellulose in the range of 8:3 to 7:3 were evaluated and it was surprisingly found that at these ratios coat rupture time of about 1 hr was obtained and the coat rupture time was not sensitive to the amount of coat applied. However, the coat did not rupture in a reliable manner as is evident from the results on the dissolution test evaluation for coat rupture time given in Table 15 below. The test was conducted in a USP type II apparatus in pH 6.8 buffer at 50 rpm.

TABLE 15

| % weight gain on application of coat of EC:HPMC ratio of 7.5:3 | No of tablets tested | Opening time (minutes) |
|---|---|---|
| 9% | 18 | 60, 53, 60, >135, 60, 58, 48, 50, >135, 50, 75, 55, 65, 64, 55, 55, 55, 48 |
| 11% | 18 | 90, 71, 78, 80, >150, 79, 60, 66, 73, 60, 91, 70, 76, 85, did not open, 76, 76, did not open |
| 14.6% | 6 | 66, 65, 78, 180, 86, 60 |

It is seen that on an average the coat rupture time meets the target rupture time of about 1 hr, however, the reliability of rupture is low in that some tablets the coat rupture is unduly prolonged. The coat composition was then kept fixed and the core composition was optimized, for example, to compositions in Examples 1 and 2, to achieve coat rupture and drug release in a reliable manner.

Comparative Example 2

The following example is generated as per example 1 of European patent 408496, equivalent to IE 902533. The tablets were made as per the following formula in Table 16 below—

TABLE 16

| Ingredients | Quantity (mg/tablet) |
| --- | --- |
| Core | |
| Diclofenac sodium | 50 mg |
| Polyvinylpyrrolidone (crosslinked) | 100 mg |
| Sodium chloride | 50 mg |
| Silica aerogel (Aerosil ® 200) | 7 mg |
| Magnesium stearate | 3 mg |
| Coating | |
| Cellulose acetate (containing 32% acetyl) | 31 mg |
| Cellulose acetate (containing 32.9% acetyl) | 32.33 mg |
| Hydroxypropyl methylcellulose | 3.33 mg |

The core components were mixed in a tumbler mixer and compressed in a tabletting press using a 8 mm concave punch. The coating components were dissolved in a mixture of methylene chloride and methanol. This solution was used to coat the cores by a fluidized bed method. Three different batches were obtained by coating the cores to a weight gain of 4% and 9.8% (by weight of the core). The tablets were then dried for 48 hours.

The tablets obtained by this formula were tested in 900 ml of water at 37° C. and the opening time is recorded in Table 17 below.

TABLE 17

| Coating (% by weight of the core) | Observations | Target opening time as per Table 1 of example 1 of IE 902533 |
| --- | --- | --- |
| 4% (before drying) | One tablet opened at about 45 minutes. Remaining tablets did not open till 3 hours and 20 minutes. | 65 minutes |
| 4% (after drying for 48 hours at 40° C.) | One tablet opened at about 30 minutes, and another opened at about 50 minutes. Remaining tablets did not open till 2 hours and 15 minutes. | 65 minutes |
| 9.8% | No tablet opened till 2 hours and 56 minutes. | 120 minutes |

The above observations indicate that the tablets obtained by the formula mentioned in IE 902533 do not provide opening of the tablets at a specific predetermined time, as claimed in the main claim of the patent, in a reliable manner.

While the invention has been described with reference to specific embodiments, this was done for purposes of illustration only and should not be considered to limit the scope of the invention.

We claim:

1. A spaced drug delivery system designed to provide desired control on the disease condition, comprising
    (a) a first time pulse release composition comprising
        (i) a core comprising one or more first therapeutically active agent(s) and a swelling agent that swells but does not gel, wherein the swelling agent is selected from the group consisting of sodium starch glycolate, sodium croscarmellose and cross-linked polyvinyl pyrrolidone, and
        (ii) a coat comprising a mixture of a water insoluble polymer and a water soluble polymer in a weight ratio comprised in a range from 6:3 to 9:3 and in a weight gain ranging from about 2% by weight to about 20% by weight of the core, wherein the coat composition forms a continuous film that surrounds the core, and wherein the water insoluble polymer is ethyl cellulose and the water soluble polymer is hydroxypropyl methylcellulose (HPMC), and
    (b) a second composition comprising one or more second therapeutically active agent(s),
    wherein the second therapeutically active agent is released as an immediate pulse upon oral administration of the spaced drug delivery system with initiation of the immediate pulse immediately upon oral administration, and
    wherein an amount of the swelling agent in the core and a ratio of the water insoluble polymer and water soluble polymers in the coat are selected so as to cause a rupture of the coat upon uptake of water, such that the first therapeutically active agent is released as a delayed pulse, wherein the coat ruptures with initiation of the delayed pulse at a rupture time which is about a predetermined time after oral administration,
    wherein said predetermined time is in a range of from about 1 hour to about 12 hour, and said rupture time has a reliability such that 36 out of 36 tablets rupture within ±50% of the predetermined time if the predetermined time is in the range of about 1 hour to about 4 hour, and within ±25% of the predetermined time if the predetermined time is in the range of about >4 hour to about 12 hour, when tested by subjecting the tablets to a USP dissolution test using an aqueous media at 37±0.5° C., in USP Type I or Type II apparatus at an rpm selected in a range from about 50 rpm to about 100 rpm, and
    wherein the first and second therapeutically active agents act on the disease condition by similar or dissimilar, but complementary mechanisms, to control the symptoms of the disease, or a measurable indicator of the disease condition, and further wherein the time of release of the two or more therapeutically active agents is designed to provide desired control on the disease condition,
    wherein the first composition does not contain the second therapeutically active agent and the second composition does not contain the first therapeutically active agent.

2. A spaced drug delivery system as claimed in claim 1, comprising
    a. a first composition comprising one or more therapeutically active antidiabetic agent(s), which is/are released as a pulse at a predetermined time after oral administration, and
    b. a second composition comprising one or more therapeutically active antidiabetic agent(s), which is/are released upon oral administration of the spaced drug delivery system.

3. A spaced drug delivery system as claimed in claim 2, wherein the antidiabetic agent in the first composition is a biguanide antidiabetic agent, and the antidiabetic agent in the second composition is a sulfonyl urea.

4. A spaced drug delivery system as claimed in claim 1 wherein the composition is effective to provide a predetermined time of about 70 min.

5. A spaced drug delivery system as claimed in claim 4, wherein the composition is effective to provide a release of therapeutically active agent as a pulse wherein 10% or less of the active ingredient at 45 min and at least 70% of the active ingredient has been released at 2 hrs when tested by subjecting the tablets to USP dissolution test using pH 6.8 buffer at 37±0.5° C., in a USP Type II apparatus at an rpm of 75.

6. A spaced drug delivery system as claimed in claim 1, wherein the core further comprises a wicking agent.

7. A spaced drug delivery system as claimed in claim 6, wherein the wicking agent is selected from microcrystalline cellulose and colloidal silicon dioxide.

8. A spaced drug delivery system as claimed in claim 1, wherein the core further comprises starch.

9. A spaced drug delivery system as claimed in claim 1, wherein the core is coated to a weight gain of about 5% to about 10%.

10. A spaced drug delivery system as claimed in claim 1, wherein the core is coated to a weight gain of about 9% to about 10%.

11. A spaced drug delivery system as claimed in claim 1 wherein the composition is effective to provide a predetermined time in the range of greater than about 4 hr to about 12 hr, wherein the 36 out of the 36 tablets rupture within ±25% of the predetermined time.

12. A spaced drug delivery system as claimed in claim 1, wherein the core further comprises water soluble compound(s) for inducing osmosis.

13. The spaced drug delivery system of claim 1, wherein the swelling agent is sodium crosscarmellose.

14. The spaced drug delivery system of claim 1, wherein the coat has an essentially uniform thickness.

15. The spaced drug delivery system of claim 1, wherein the core contains at least one of sodium starch glycolate in an amount of from 0.5% to about 40% by weight of the core, sodium croscarmellose in an amount of from about 0.5% to about 50% by weight of the core, and cross-linked polyvinyl pyrrolidone in an amount of from 0.5% to about 5% by weight of the core.

* * * * *